United States Patent [19]

Sakuma

[11] Patent Number: 4,861,554
[45] Date of Patent: * Aug. 29, 1989

[54] AUTOMATIC ANALYZING APPARATUS FOR ANALYZING AGGLUTINATION PATTERNS

[75] Inventor: Hajime Sakuma, Hachioji, Japan

[73] Assignee: Olympus Optical Co., Ltd., Tokyo, Japan

[*] Notice: The portion of the term of this patent subsequent to Feb. 23, 2005 has been disclaimed.

[21] Appl. No.: 36,210

[22] Filed: Apr. 8, 1987

Related U.S. Application Data

[63] Continuation of Ser. No. 741,728, Jun. 6, 1985, abandoned, which is a continuation of Ser. No. 448,327, Dec. 9, 1982, abandoned.

[30] Foreign Application Priority Data

Dec. 14, 1981 [JP] Japan ............................ 56-200062
Dec. 15, 1981 [JP] Japan ............................ 56-200818
Dec. 15, 1981 [JP] Japan ............................ 56-200824

[51] Int. Cl.⁴ .................................................. G01N 35/04
[52] U.S. Cl. ........................................ 422/65; 422/67; 422/73
[58] Field of Search ................................ 422/63–67, 422/73, 102, 104; 435/291

[56] References Cited

U.S. PATENT DOCUMENTS

| 3,193,358 | 7/1965 | Baruch | 422/67 |
|---|---|---|---|
| 3,489,521 | 1/1970 | Buckle et al. | 422/65 |
| 3,617,222 | 11/1971 | Matte | 422/23 |
| 3,708,264 | 1/1973 | Jottier | 422/81 |
| 3,776,700 | 12/1973 | Gallant | 422/65 |
| 3,883,305 | 5/1975 | Hoskins et al. | 422/65 |
| 3,897,216 | 7/1975 | Jones | 422/67 |
| 4,058,367 | 11/1977 | Gilford | 422/73 |
| 4,130,395 | 12/1978 | Chryssanthou | 422/63 |
| 4,154,795 | 5/1979 | Thorne | 422/102 |
| 4,319,882 | 3/1982 | Sharma | 422/73 |
| 4,459,265 | 7/1984 | Bergland | 422/65 |
| 4,466,740 | 8/1984 | Kano et al. | 422/73 |
| 4,483,927 | 11/1984 | Takakawa | 422/65 |
| 4,727,033 | 2/1988 | Hijikata et al. | 422/73 |

FOREIGN PATENT DOCUMENTS 48-33148 10/1973 Japan.
55-711951 5/1980 Japan ................................ 422/65

*Primary Examiner*—Michael S. Marcus
*Attorney, Agent, or Firm*—Arnold, White & Durkee

[57] ABSTRACT

An automatic analyzing apparatus for analyzing agglutination patterns produced in response to an immunological agglutinating reaction is disclosed. The apparatus comprises a device for carrying a plurality of sample tubes which accommodate blood samples to be analyzed therein at a delivery position in order, a device for forming a plurality of diluent blood samples by diluting the blood samples in the tubes at the delivery position, and a device for transporting microplates having blood samples and reagents delivered in the reaction vessels along the line in a substantially stationary manner.

6 Claims, 10 Drawing Sheets

FIG_6
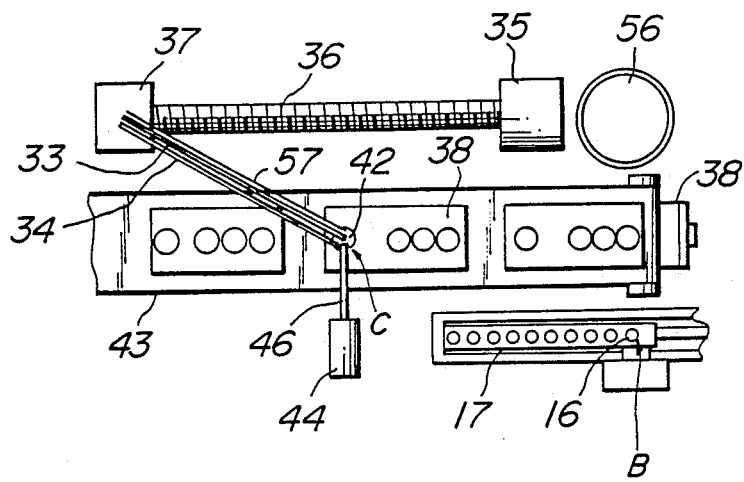
FIG_7
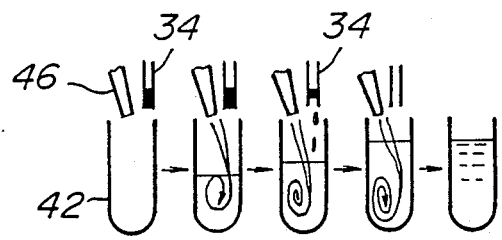
FIG_8
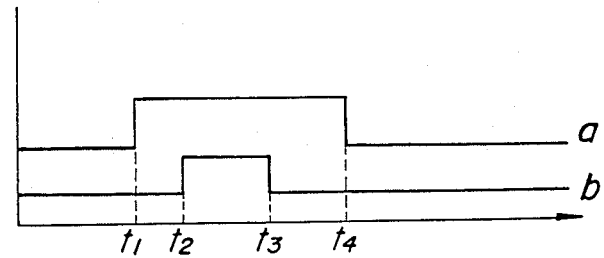

FIG.12
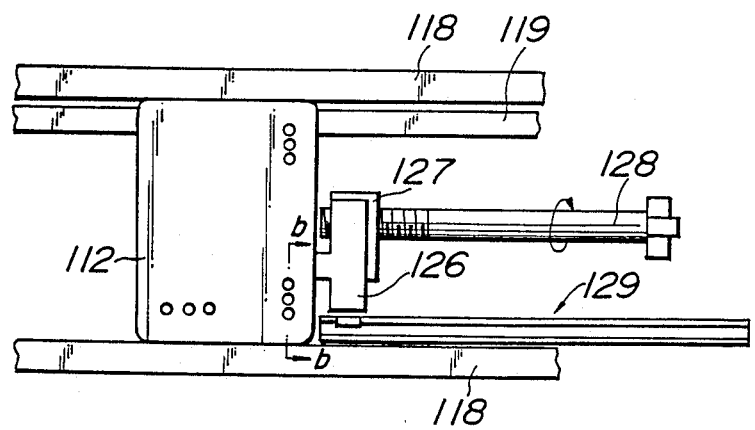
FIG.13a
FIG.13b
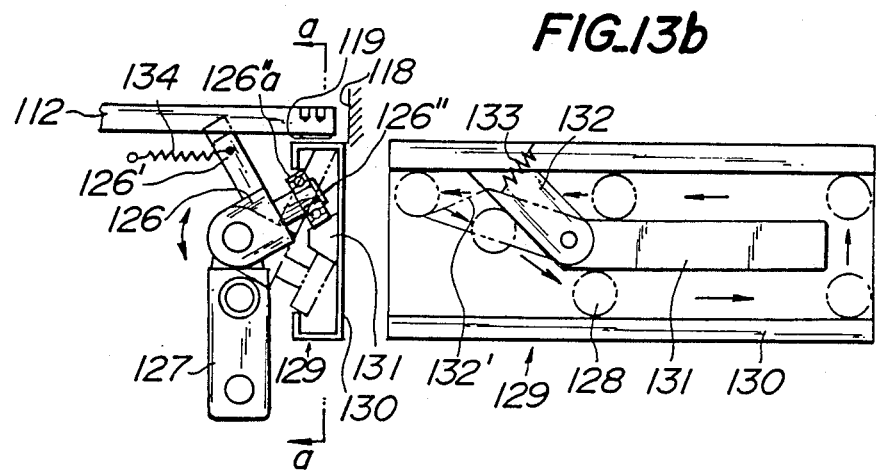

AUTOMATIC ANALYZING APPARATUS FOR ANALYZING AGGLUTINATION PATTERNS

This is a continuation of application Ser. No. 741,728 filed June 6, 1985, which in turn is a continuation application of Ser. No. 448,327 filed Dec. 9, 1982, both abandoned.

BACKGROUND OF THE INVENTION

This invention relates to an apparatus for analyzing agglutination patterns produced in response to an immunological agglutination reaction, and more particularly to apparatus for identifying various kinds of blood types with the aid of agglutination patterns of blood corpuscles or for detecting various kinds of antibodies and various antigens in sample solutions (like viruses, proteins or the like) with the aid of agglutination patterns of not only blood corpuscles but also of particles of materials such as latex, carbon or the like.

In known analyzing apparatus due to the agglutinating reaction, reaction vessels and analyzing steps are different for respective components to be analyzed. For instance, in a known manual apparatus for judging the blood type of ABO system, use was made of test tubes as the reaction vessels. In this apparatus a sample blood is first centrifuged to separate red blood cells and serum from each other, and then a given amount of blood cells is mixed with a diluent to form a blood cell suspension of 2 to 5%. Then, a given amount of the blood cell suspension is delivered into a test tube into which anti-A-serum of anti-B-serum is also distributed. After the blood cells have been centrifuged, the test tube is shaken and it is confirmed with the naked eye whether or not agglutination is formed. In this case, the sample blood which produces agglutination together with A-type antibody, but does not produce agglutination together with B-type antibody is identified as A-type, the sample blood which produces agglutination exclusively with B-type antibody is judged to be B-type, the sample blood which forms agglutination with both A-type and B-type antibodies is determined to be AB-type, and sample blood which does not produce agglutination with either A-type and B-type antibodies is judged as O-type.

In order to detect and measure HBs antigen, a method has been proposed which makes use of a plastic plate, called a microplate, provided with a number of wells, i.e. reaction vessels each having a conical base surface. This conventional method makes use of a microplate having 10×12 wells, for example, and detects and prescribes the HBs antigen by the following procedure.

(1) Buffer solution specially prescribed for R-PHA method is introduced into each well of the microplate one drop (0.025 ml) at a time.
(2) A test serum (0.025 ml) is added to the first well of a row. By using a diluter, the doubling dilution is performed along the row up to the last (tenth) well.
(3) One drop of R-PHA buffer (0.025 ml) is added to a first row and one drop of R-PHA inhibition solution is added to a second row.
(4) After the mixtures thus treated have been sufficiently agitated by a micromixer for 10 seconds, incurvation is effected for one hour at 37° C.
(5) A drop of R-PHA cells of 1% suspension (0.025 ml) is added to each well.
(6) The mixtures are agitated by the micromixer for ten seconds to suspend the R-PHA cells uniformly.
(7) After the mixtures thus treated have been made stationary at room temperature for one hour, agglutination patterns are detected.

In the T-PHA system for syphilis, different diluents of a sample serum are formed in the microplate and a reagent prepared by bonding syphilis viruse with red blood cells of sheep is added to the serum diluents. After natural segmentation, it is confirmed with naked eyes whether or not agglutination is formed.

As described above, in the analyzing apparatuses due to immunological agglutination reaction different kinds of reaction vessels are used depending upon the test items and further successive steps are also different for respective items.

There has also been known a microtitor apparatus in which use is made of the microplate as the reaction vessels and steps are partially automated. In this apparatus, delivery of samples and reagents and detection of agglutination are carried out automatically, but other steps are effected manually. This is due to the fact that in the case of using the microplate, mechanism and operations are liable to be complicated and thus, it is extremely difficult to effect all the steps automatically. Further, the microtitor method has several disadvantages. Since the sample serum is delivered quantitatively with the aid of capillary phenomenon, it is necessary to first deliver diluent into each well in the microplate and then a tip of dilutor onto which a sample has been applied is immersed into the diluent to mix the serum and diluent. Such a step is very complicated as compared with normal delivery steps in the analyzing apparatuses and thus could be controlled only by means of complicated mechanisms. Further, the delivery amount is made always constant, because the capillary action is utilized and thus, the delivery amount could not be adjusted at will. Further, the mixed solution is applied to the dilutor and the sample is partially wasted. This becomes a serious drawback in a multi-item analyzer.

Moreover, if the delivery of the blood cell sample is effected before the serum sample delivery, an indefinite amount of the blood cell sample might be removed from the well. Therefore, in the microtitor system, the diluent delivery, serum delivery and blood cell delivery have to be performed in this order and thus, the mechanical arrangement or design might be restricted. Further in the microtitor method, since use is made of the blood cell suspension of about 1%, the operation is liable to be very complicated as compared with the test tube method described above.

In a conventional method of identifying blood types, for example, which has heretofore been proposed, use was made of a winecup-shaped reaction vessel into which was quantitatively introduced a sample solution, i.e. 2 to 5% of test blood corpuscles suspended in saline solution, and a specified antiserum, i.e. anti-A- or anti-B-serum. Then, the mixture was held stationary for reaction between blood corpuscles and antiserum. Subsequently, it was centrifuged to sediment blood corpuscles. Then, the reaction vessel was rapidly wobbled such that the sedimented blood corpuscles were forcedly separated one from the other and then relatively slowly wobbled so as to collect the clumped compositions in the center portion of the base surface of the vessel and form settling patterns, thereby photometrically detecting these patterns.

Such conventional blood type identifying method in which sedimentation is effected and then the reaction vessel is rapidly wobbled so as to separate the sedimented blood corpuscles from the base surface of the vessel can only be applied to the analysis of regular ABO blood type, which shows stong agglutination, but could not be applied to many other immunological agglutination reactions which show weak agglutination, for example, a method of determining Rh blood subtype or detecting various kinds of incomplete antibodies. That is, if the agglutination reaction is weak, the blood corpuscles or the like which have been clumped together become separated one from other when the reaction vessel is wobbled, and as a result, the particles are not collected in the center portion of the reaction vessel.

Further, in this known apparatus, in order to effect the accurate judgement of the blood type, it is necessary to prepare a substantial amount of the sample blood cells and thus, required amounts of standard antiserums are increased accordingly. Nowadays, a very large number of test items are to be effected for respective patients and thus, required amounts of the sample blood for respective items must be decreased as small as possible.

In known analyzing apparatus due to the agglutinating reaction, the reaction line for holding microplate over the time necessary to reaction has horizontally arranged microplates which are transported in the vertical direction by the belt conveyor so that the apparatus becomes large in construction, and dusts or the like are fallen on the microplate because of planer arrangement resulting in an affection in judgement. In order to form the reaction patterns the plate must be placed quietly, but the plate is transported in turn even during plate holding thereby subjecting it to vibration from the belt resulting in an affection of reaction pattern formation.

In the case of the direct judgement of ABO blood type blood cells are used as sample and in the case of the indirect judgement of ABO blood type and the analysis of antibody screening serums are used as sample. In this case the concentration of blood cell suspension is 1.5% and the concentration of serum is 25% so that the blood cell suspension has very high diluting magnification. In case of forming the diluted suspension having high diluting magnification there is no problem when the suspension is completely agitated by hand, but in the automatic analyzing apparatus diluted suspension of required concentration cannot often be obtained since a part of blood cell adhered to the wall of vessel. In the automatic analyzing apparatus the delivering amount of blood cell suspension and serum diluent for judgement and analysis is very small, such as 25 $\mu$l so that the effect of blood cell amount in the delivered blood cell suspension on agglutination reaction becomes large resulting in a cause of erroneous judgement. If agitating device is provided in the automatic analyzing apparatus the above problem can be solved, but the apparatus becomes complicated in construction and expensive.

The method of feeding sample vessels in the known apparatus comprises the steps of directly housing a plurality of sample vessels in each partition of cassette trays partitioned into a plurality of partitions, conveying these sample vessels into the automatic analyzing apparatus by means of the belt conveyor, after a predetermined work on samples in the sample vessels in the automatic analyzing apparatus, sending the used sample vessels into another empty cassette tray arranged at the end opposite to the sample vessel supply side of the belt conveyor.

In the method of feeding sample vessels in this known automatic analyzing apparatus, however, there are required both the cassette tray for feeding sample vessels to the belt conveyor and the empty cassette tray for housing the used sample vessels discharged from the belt conveyor, so as to occupy much space and to enlarge the whole apparatus. In relation to the work for treating samples in the automatic analyzing apparatus, the cassette tray on the feed side of the sample vessel is usually positioned apart from the cassette tray on the discharge side of the used sample vessel, and as a result, it is necessary to connect therebetween another transporting mechanism, which makes the construction of the apparatus complicated.

SUMMARY OF THE INVENTION

It is an object of the present invention to overcome the above described disadvantages of the conventional automatic analyzing apparatus.

It is another object of the present invention to provide an automatic apparatus for analyzing agglutinating patterns in which a sample vessel feed mechanism and a sample vessel delivery mechanism to the automatic analyzing apparatus can be miniaturized and the used sample vessels can efficiently be treated without taking any space.

It is other object of the present invention to provide an automatic apparatus for analyzing agglutinating patterns in which blood cell suspension having predetermined and low concentration can easily and surely be formed by performing agitation with diluent without adhering blood cell to the vessel wall.

It is further object of the present invention to provide an automatic apparatus for analyzing agglutinating patterns in which the apparatus comprises a microplate transporting device capable of performing feeding of microplates to the apparatus, stopping of the plate at reagent and sample delivery positions, holding of the plate over the time necessary to reaction, stopping of the plate at measuring position, sending of the plate to visual observation place, and discharge of the plate according to analyzing order, and having small occupied area of reaction line as well as capable of solving the dust and vibration problems.

According to the present invention there is provided an immunological agglutination reaction analyzing apparatus comprising:
  means for carrying a plurality of sample tubes which accommodate blood samples to be analyzed therein at a delivery position in turn,
  means for forming a plurality of diluent blood samples by diluting the blood samples accommodated in the sample tubes at the delivery position,
  a reactive reaction line including a plurality of reaction line passages,
  means for feeding microplates successively from input side of the reaction line,
  means for delivering given amounts of the diluted blood samples into at least one reaction vessel of the microplates supplied to the reaction line,
  means for delivering given amounts of the reagents into the reaction vessels according to analysis-items,
  means for transporting microplates having blood samples and reagents delivered in the reaction vessels along the reaction line in a substantially non-vibrating manner, means for photoelectrically detecting agglutination patterns formed on the bottom surfaces of the reaction vessels at the predetermined position of the reaction line by subjecting to antigen and antibody combination reaction during transporting the blood sample and the reagent along the reaction line in a substantially non-vibrating manner after delivering thereinto the reaction vessels, means for receiving the detection signal to effect an analysis due to the existence or non-existence of the agglutination patterns, and means for discharging the microplates from an exit of the reaction line after the agglutination patterns of all the reaction vessels in the microplate have been detected.

The means for carrying a plurality of sample tubes is a rack supplying or feeding device for supplying, in turn, racks from a cassette tray having a plurality of vessels accommodating samples to be analyzed therein, the device comprises means for intermittently sending the cassette tray on a rack transporting mechanism one partition by one partition, means for sending racks housed in a selected partition of the cassette tray into the analyzing apparatus by the rack transporting mechanism, and means for backing the rack to the selected partition of cassette trays by the rack transporting mechanism after subjecting the vessels housed in the rack to predetermined operations in the apparatus thereby sending next cassette tray on the rack transporting mechanism one partition by one partition.

Means for forming a plurality of diluent blood samples is means for forming blood cell suspension used for immunological agglutinating reaction, and diluent solutions are delivered at the same time or before blood cell solutions of a patient is delivered in a vessel for diluent solution.

The microplate transporting device comprises a microplate feeding means for feeding respective vessels of the microplate to required delivering position, a delivery transporting means for transporting respective trains of reaction vessel to a required delivery position, first sending means for sending delivered microplate to a reaction line transporting means, a reaction line transporting means for receiving microplates in turn in the horizontal state and for intermittently transporting the microplates in the vertical direction, a measurement transporting means for transporting the microplate to a measuring position from the reaction line, and a second sending means for sending measured microplate to a discharging position.

BRIEF DESCRIPTION OF THE DRAWINGS

FIG. 6 is a diagrammatic plan view illustrating status of delivering into the diluent vessel blood cell sample of the apparatus shown in FIG. 4;

FIG. 7 is a diagrammatic side view showing steps of forming blood cell suspension in turn;

FIG. 8 is a graph illustrating relation between diluent delivering step and blood cell sample delivering step shown in FIG. 7;

FIG. 12 is a plan view illustrating first sending means for supplying to the reaction line the delivered microplate of the apparatus shown in FIG. 9;

FIG. 13a is a sectional view taken on line b—b in FIG. 12;

FIG. 13b is a sectional view taken on line a—a in FIG. 13a;

DESCRIPTION OF THE PREFERRED EMBODIMENT

Figure 1:
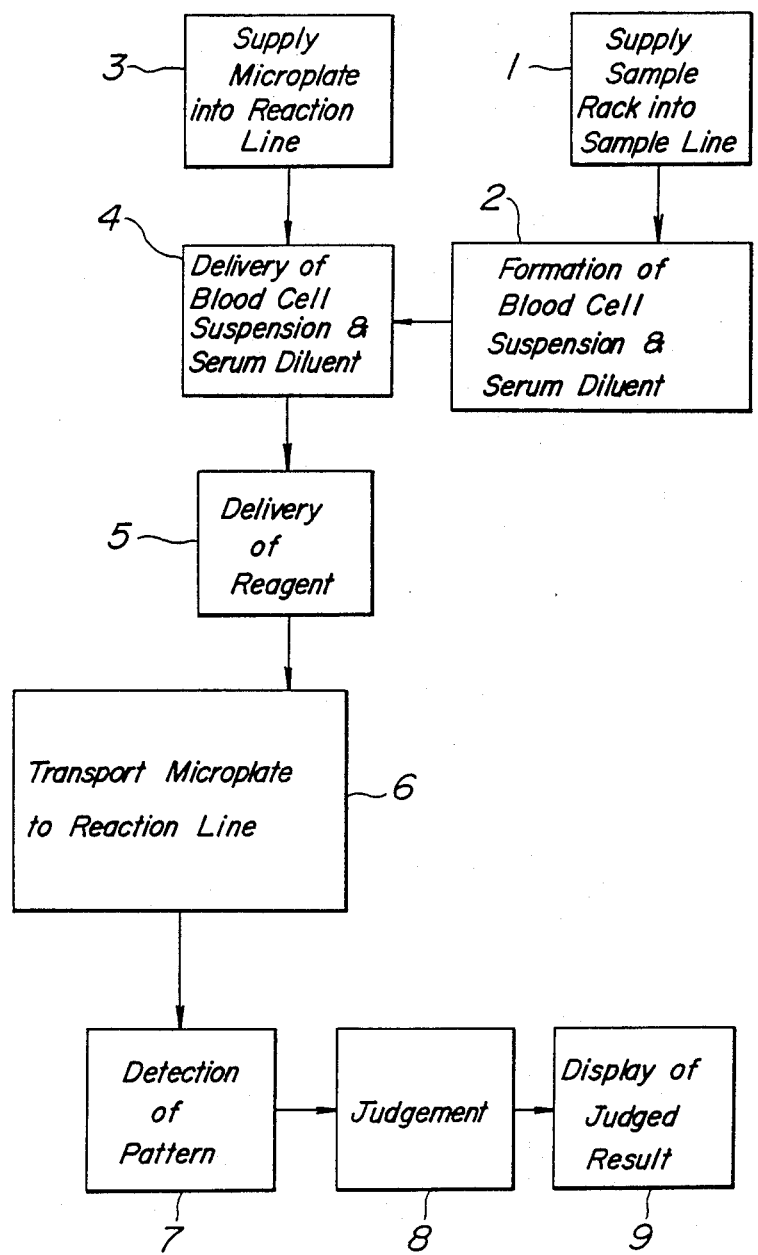
FIG. 1 is a block diagram showing successive operations of an embodiment of the analyzing apparatus according to the present invention.

FIG. 1 shows successive operations of one embodiment of an automatic analyzing apparatus according to the present invention.

In section 1 sample racks having a plurality of sample tubes which accommodate blood samples to be analyzed therein are automatically fed into a sample line, so that the sample tubes are carried to a section 2 at the delivery position in turn. In the section 2 the blood samples accommodated in the sample tubes are diluted by saline solution to form a plurality of diluent blood samples such as a blood cell suspension. In this step serum diluent is also provided at the delivery position. These blood cell suspension and serum diluent are delivered into reaction vessels of microplates in a section 4.

The microplates are provided with a plurality of empty reaction vessels and fed into a reaction line at a section 3. Given amounts of reagents are delivered into the reaction vessels having delivered blood cell suspension and serum diluent therein at a section 5 in accordance with analysis items. The microplates having blood sample and reagents in the reaction vessels are transported along the reaction line in a substantially non-vibrating manner at a section 6. In a section 7 agglutination patterns formed on the bottom surface of the reaction vessels are photoelectrically detected to generate electrical signals, An analysis of agglutination patterns is effected by these signals to judge various test items in a section 8 and the result judgement is displayed at a section 9.

In an embodiment of the present invention, there is explained a device for supplying or feeding racks to the automatic analyzing apparatus for carrying out judgement of blood type, Rh judgement, antibody screening, syphilis inspection and HBs antigen inspection by an immunological agglutination reaction.

Figure 2:
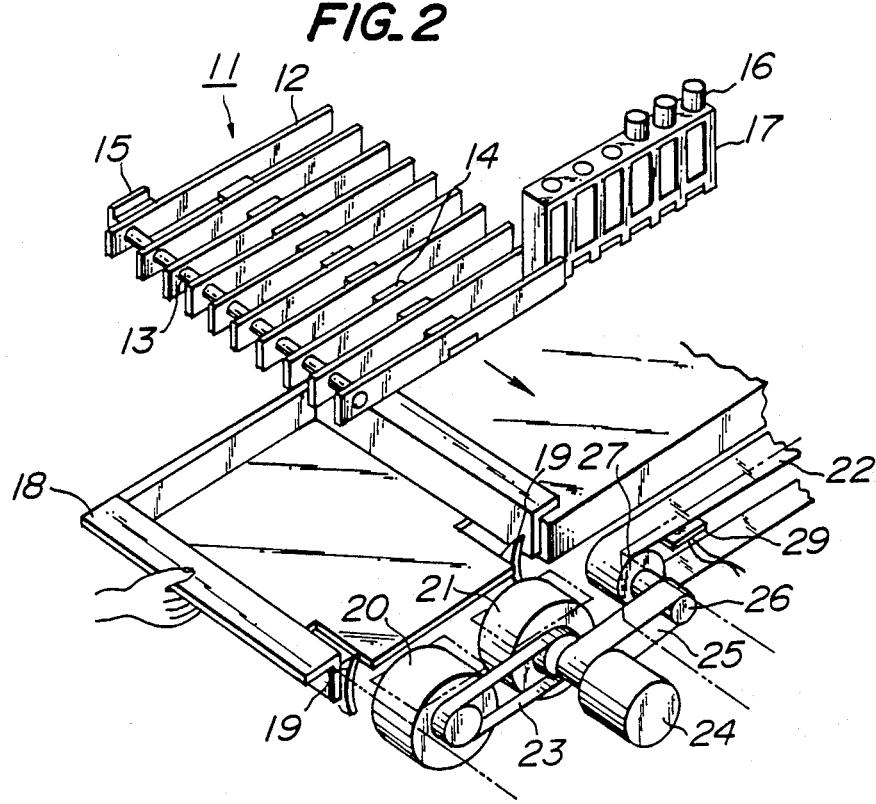
FIG. 2 is a partially cutaway perspective view showing a construction of a rack transporting mechanism used in a rack feeding section of the automatic analyzing apparatus according to the present invention.
Figure 3:
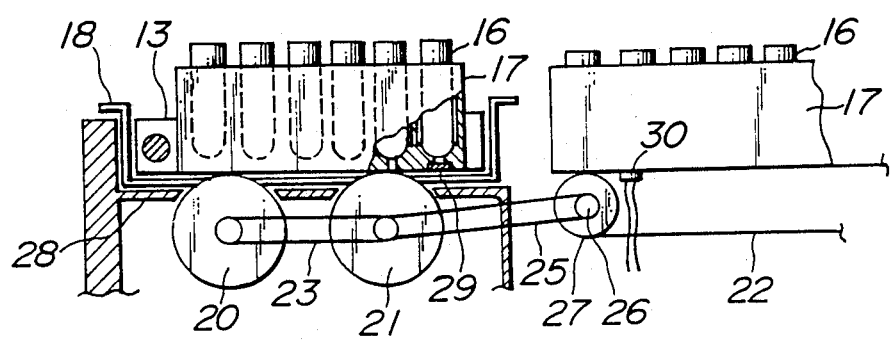
FIG. 3 is a partially cutaway sectional view illustrating status of feeding racks in the analyzing apparatus by the rack transporting mechanism shown in FIG. 2.

FIGS. 2 and 3 show the construction of a rack for housing sample vessels and of a cassette tray for housing the rack and the mechanism for transporting racks into the automatic analyzing apparatus. In FIG. 2, a cassette tray 11 comprises a plurality of partitions 12 arranged upright in the perpendicular direction by keeping a certain gap, a first correction member 13 for connecting one side end of these partition plates 12, a second connection member 14 for connecting the bottoms of the partition plates 12 by leaving some clearance for operating a rack transporting mechanism from the bottom portion of the partition compared from the partition plates 12, and a knob 15 provided outside the last partition plate 12 in the transporting direction of the cassette tray 11. A rack 17 in which is placed a plurality of sample vessels 16 is accommodated in each partition of the cassette tray 11 one by one. The cassette tray 11 is used by accommodating in a cassette tray receiver 18, so that each rack 17 is fitted into cassette tray 11 by dropping into to each partition of the cassette tray 11 housed in the cassette tray receiver 18. The cassette tray receiver 18 has notches 18a on both sides on the bottom surface of the end portion in the transporting direction of the cassette tray 11, and a pawl 19 is projected into the cassette tray receiver 18. This pawl 19 intermittently transports every one partition of the cassette tray 11 in the direction of an arrow A shown in FIG. 2. The rack 17 accommodated in the partition transported by the pawl 19 of the cassette tray 11 is sent to the right in FIGS. 2 and 3 by rollers 20, 21, received by a belt 22 and sent into the automatic analyzing apparatus. The rollers 20, 21 are connected by a belt 23 and driven by a motor 24 directly connected to an axis of the roller 21. The belt 22 is driven by the motor 24 through a belt 25, a shaft 26 and a pulley 27, so that the rollers 20, 21 and the belt 22 can be driven by interlocking with the motor 24. FIG. 3 shows the state of setting the cassette tray 11 under the condition of accommodating in the cassette tray receiver 18 on a rack supply or feed portion 28 of the automatic analyzing apparatus. From this condition, the cassette tray 11 is sent to the rollers 20, 21 one by one by the pawl 19 shown in FIG. 2, and the rack 17 housed in the cassette tray 11 is sent into the automatic analyzing apparatus. As shown in FIG. 3, a permanent magnet 29 is embedded in the lower portion of the foremost sample vessel receiving portion of the rack 17 in the rack transporting direction, and in case of sending the rack 17 into the automatic analyzing apparatus by the belt 22, the permanent magnet 29 is inspected by a reed relay 30 provided at the lower portion of the belt 22, and the passage of the rack 17 is confirmed.

Figure 4:
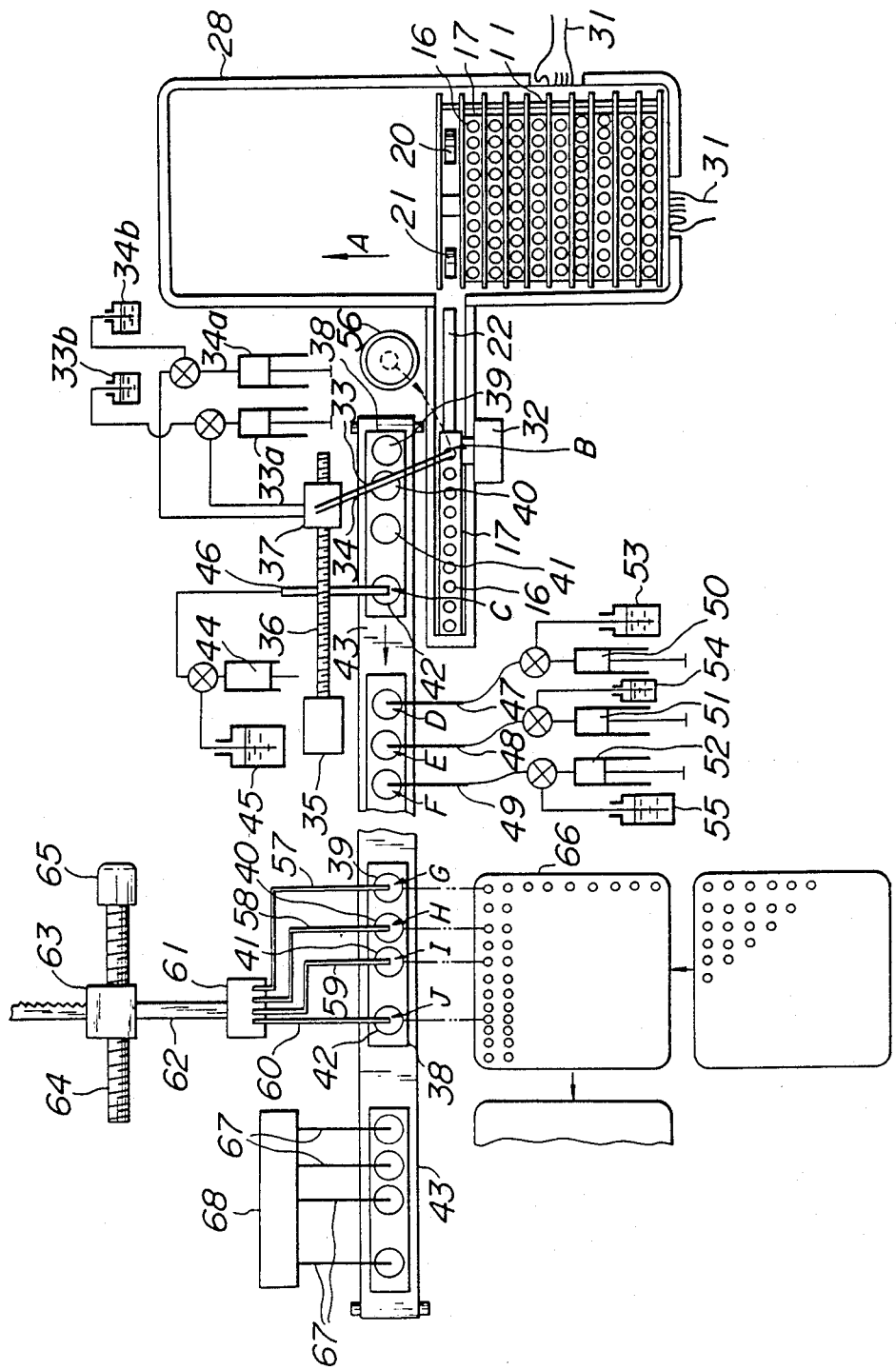
FIGS. 4 and 5 are diagrammatic plan views illustrating the rack feeding section of the apparatus having rack transporting mechanism shown in FIGS. 2 and 3.
Figure 5:
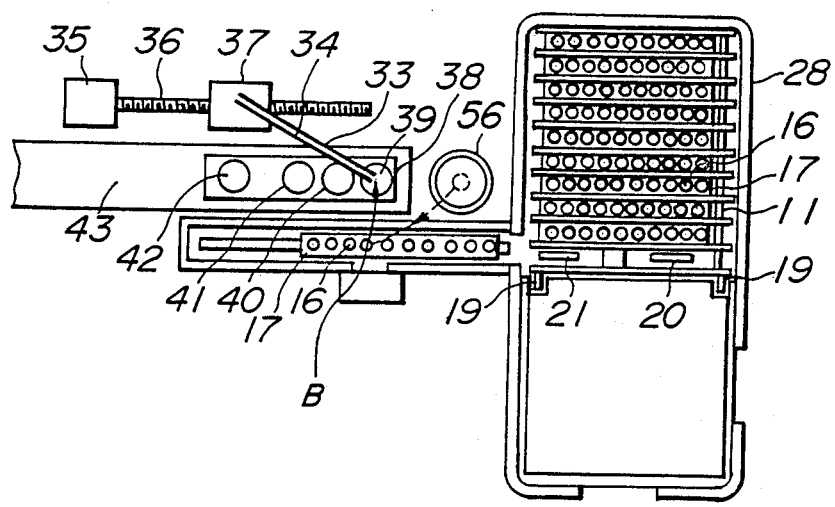

FIGS. 4 and 5 illustrate the automatic sample rack supplying section, the test sample preparing section for making the blood cell test sample and serum test sample and the test sample delivering section for delivering the blood cell test sample and serum sample into reaction cells found in the microplate. In FIG. 4, the sample vessel 16 placed on the rack 17 contained sample blood separated into two layers of blood cells and serum by centrifuge. The cassette tray 11 containing the racks 17 together with the cassette tray receiver 18 is set at a rack supply section 28 of the automatic analyzing apparatus main body by hands 31. The cassette tray 11 is thereafter moved to the direction of an arrow A by the pawl 19 shown in FIG. 2, and the first partition of the cassette tray 11 is transported and stopped on the rollers 20, 21. The first rack 17 housed in the first partition of the cassette tray 11 is then transported to the left in FIG. 4 by driving the rollers 20, 21 and the belt 22. The rack 17 is intermittently transported by the belt 22 with a pitch corresponding to a distance between successive sample vessels 16 and is stopped at a sample sucking position B for a certain time. During the period of stopping the rack 17 at the position B, an ID mark, a subject, its number, measuring items and the like, put on an outer wall of the sample vessel 16 as bar codes are optically read by an ID reader 32 and stored in a memory, and the following analyzing treatment to be effected by the automatic analyzing apparatus is controlled by the stored data. At the same time, during the period of stopping the rack at the position B, sample delivery nozzles 33, 34 are lowered in the sample vessel 16 and a predetermined amount of serum is sucked into the nozzle 33 by a syringe 33a, and a predetermined amount of blood is sucked into the nozzle 34 by a syringe 34a. In case of sucking the sample, the liquid surface of the sample and the boundary surface between serum and blood are detected by detecting a resistance change by means of an electrode (see FIG. 6) provided adjacent the nozzles 33, 34. After sucking the serum and blood, these nozzles 33, 34 are raised and simultaneously rotated in the counterclockwise direction as shown in FIG. 4, while a screw shaft 36 is rotated by a reversing motor 35, a nozzle holder 37 is moved to the left shown in FIG. 4, and the ends of the nozzles 33, 34 are positioned above a diluting vessel 39 placed on a block 38. Four diluting vessels 39, 40, 41, 42 are placed on each block 38, and the block 38 is mounted on an endless belt 43 and is moved to the left in FIGS. 4 and 5 by the belt 43. In the diluting vessel 39 a predetermined amount of serum is delivered from the nozzle 33. Then the screw shaft 36 is rotated by the motor 35 to move the nozzles 33, 34 in the left shown in FIG. 4 and successively stopped above the diluting vessels 40, 41 to deliver predetermined amounts of serum into the vessels 40, 41 from the nozzle 33. In this manner the serum sample is delivered in the diluting vessels 39, 40, 41. After delivering the serum, the nozzles 33, 34 are further moved to the left in FIG. 4 and stopped at a position C above the diluting vessel 42, and a predetermined amount of blood cells is delivered into the diluting vessel 42 from the nozzle 34. Simultaneously with delivery of the blood cells, a predetermined amount of a diluent in a diluent vessel 45 is sucked by a syringe 44, and then is discharged into the diluting vessel 42 by a nozzle 46 to form a blood cell suspension. The delivery of this diluent is started at the same time or before the delivery of the blood cells and finished after completing the delivery of the blood cells. This is for preventing the blood cells from adhering onto the diluting vessel 42 and for stirring the blood cells and the diluent effectively. This will be further explained in detail later on. In this manner, the discharge and delivery of the serum and blood cells from the same subject are completed. Then, the block 38 is moved to the left in FIG. 4 by driving the belt 43, and a next block 38 is arranged at the position for delivery of a next sample. At that time, the diluting vessels 39, 40, 41 on the block 38 are moved into positions D, E and F underneath nozzles 47, 48, 49, respectively. Diluents in diluent vessels 53, 54, 55 are sucked by syringes 50, 51, 52 connected to these nozzles, respectively and predetermined amounts of the diluents are delivered from the nozzles 47, 48, 49 to the diluent vessels 39, 40, 41, respectively to form three kinds of serum test samples. Many test items can be tested with the thus formed one kind of a blood cell test sample and three kinds of serum test samples. An example of these test items is shown in the following Table 1.

TABLE 1

| Item | Kind of Diluent | Vessel |
| --- | --- | --- |
| Rh judgement | Blood cell suspension (diluted with physiological saline solution) | 42 |
| ABO direct judgement | | |
| ABO indirect judgement | Serum diluent (diluted with physiological saline solution) | 41 |
| Antibody screening | | |
| HBs antigen inspection | Serum diluted (diluted with R-PHA buffer) | 40 |
| Syphilis inspection | Serum diluted (diluted with T-PHA buffer) | 39 |

After completing the discharge and delivery of blood cells from the nozzle 34, the motor 35 is driven to move the nozzle holder 37 to the right in FIG. 4 and the nozzles 33, 34 are rotated counterclockwise to locate their tips above a washing liquid tank 56. Then the tips and lowered and outer walls of the nozzles 33, 34 are washed in the washing liquid tank 56. At the same time, washing liquid in washing liquid vessels 33b, 34b is sucked by the syringe 33a, 34a and discharged from the nozzle 33, 34 to wash the inner surfaces of the nozzles 33, 34. After completing washing, the nozzles 33, 34, are pulled up from the washing liquid tank 56, rotated in the clockwise direction in FIG. 4, and one cycle step of delivery of the sample to the diluting vessels is completed. During this one cycle, the rack 17 is moved by one pitch by means of the belt 22, and the next sample vessel 16 placed on the rack 17 is stopped at the sucking position B. Thus the rack 17 is intermittently moved in synchronism with delivery of the sample, and when all the samples in the sample vessels 16 placed on the rack 17 are delivered, the belt 22 and the rollers 20, 21 are reversed so as to return the rack 17 to the original partition on the cassette tray 11. Then the cassette tray 11 is advanced by one pitch in the direction A by the action of the pawl 19 and the rack 17 housed in the next partition is sent onto the rollers 20, 21 and is sent to the automatic analyzing apparatus. In this manner, the rack 17 housed in successive partitions of the cassette tray 11 is sent to the automatic analyzing apparatus, and when the rack 17 housed in the last partition is sent to the automatic analyzing apparatus as shown in FIG. 5, the operator brings the cassette tray 11 back to the receiver while the samples in the sample vessels 16 placed on the last rack 17 are delivered, and the cassette tray is exchanged with a new cassette tray 11 with no rack in the first partition of the cassette tray 11 as shown in FIG. 4. Wereby, the rack 17 sent from the cassette tray 11 before exchange is housed in the first partition of the new cassette tray 11, and the next rack 17 can be sent to the automatic analyzing apparatus from the second partition. Hence, the racks can be successively supplied to the automatic analyzing apparatus without interruption, so that there is no delay of operating cycle of the apparatus and the delivery action. It usually takes two minutes and thirty seconds from delivery of the rack 17 from the cassette tray 11 to the automatic analyzing apparatus to redelivery of the rack, so that it is possible to exchange the cassette tray 11 within one to two minutes by taking some allowance after delivering the rack 17 from the last partition of the cassette tray 11.

A jam alarm in case of supply and delivery of the rack 17 will be explained next. In FIG. 3, as explained in the foregoing, the permanent magnet 29 is embedded in the bottom portion of the first sample vessel receiving portion of the rack 17, and when the rack 17 is transported into the automatic analyzing apparatus by the belt 22, the reed relay 30 inspects the magnet 29, which signal actuates a timer (not shown). After completing delivery of the sample in the sample vessel 16 placed on the rack 17, the magnet 29 again crosses the upper portion of the reed relay 30 and actuates the reed relay 30. If the time from the first actuation of the reed relay 30 to the next actuation is within a setting time of the timer, it is judged that the rack 17 is normally transported and no alarm is generated, but if this time is more than the setting time, it is judged as a jam of the rack 17, an alarm is generated and the rack 17 is stopped.

In the method of supplying racks to the automatic analyzing apparatus according to the invention, the cassette tray housed the rack therein before delivery of the sample and the cassette tray housed the rack after delivery of the sample therein can be used in common, while the rack before use can be supplied and the rack after used can be received at the same position, and as a result, both the rack transporting mechanism and the automatic analyzing apparatus can be made compact, the cassette tray housed the used rack therein can be exchanged with the cassette tray housed rack therein before use without interrupting the delivery action of the sample by the automatic analyzing apparatus and the analyzing cycle of the whole apparatus, and judgement whether the rack housed in the cassette tray is already analyzed or not yet analyzed can easily be distinguished by whether the first partition of the cassette tray is empty or the last partition thereof is empty.

Now the test sample preparing operation will be further explained in detail with reference to FIGS. 6 to 8. It should be noted that in FIG. 4 the motor 35 is provided at the left end of the screw 36, but in FIG. 6 the motor is provided at the right end of the screw. After a given amount of the blood cells in the sample vessel 16 situating at the position B has been sucked into the nozzle 34, the nozzle tip is placed above the delivery position C as shown in FIG. 6. Then the diluent is started to be discharged from the nozzle 46 by means of the syringe 44 at a timing $t_1$ shown in FIG. 8. Then at a timing $t_2$ which the diluent is discharged into the diluting vessel 42, the blood cells are discharged from the nozzle 34. This discharge of the blood cells is continued until a timing $t_3$ and at this timing $t_3$ the diluent is still discharging. At a timing $t_4$ after the completion of discharge of blood cells, the discharge of the diluent is stopped. FIG. 7 shows the above operations schematically at successive timings $t_1$ to $t_4$. In FIG. 8 a waveform a indicates the driving signal for the diluent discharging syringe 44 and a waveform b the driving signal for the blood cell discharging syringe 34a.

In the above diluting operation, since the blood cells are delivered into the vessel 42 while the diluent is continuously discharged into the vessel 42, the blood cells are sufficiently stirred and mixed by means of a circulating flow of the diluent and further they are hardly adhered onto the inner wall of vessel 42. Therefore, it is possible to prepare the uniform blood cell test sample having a precisely predetermined concentration. In this case, it is preferable to arrange the tip of the nozzle 46 slightly lower than the tip of the nozzle 34, because the diluent is not projected upon the outer surface of the nozzle 34.

Now the mechanism for delivering the test samples prepared in the diluting vessels 39 to 42 into the reaction vessels in the microplate will be explained with reference to FIG. 4. After diluting the serum samples at the positions D to F, the belt 43 is driven to move the support 38 to the left in FIG. 4 and the diluting vessels 39 to 42 are stopped at delivery positions G to J, respectively. At these positions test sample delivery nozzles 57 to 60 are arranged and these nozzles are mounted on a nozzle supporting plate 61 which is secured to an end of a rod 62. The rod 62 is mounted on a block 63 movably up and down in FIG. 4. This movement of the rod may be effected by means of a rack and pinion mechanism. The block 63 is mounted on a screw 64 which is rotated by a reversal motor 65. Therefore, by driving the motor 65 the block 63 and thus the nozzles 57 to 60 can be moved right and left in FIG. 4.

When the nozzles 57 to 60 are in the positions G to J, respectively as shown in FIG. 4, the nozzles is moved downward until their tips are immersed into the test samples in the vessels 39 to 42 by a given depth. Then, syringes connected to the nozzles 57 to 60 are driven to suck given amounts of the diluted test samples into the nozzles. After the nozzles are moved upward, the rod 62 is moved toward the belt 43 and nozzle tips are brought into delivery positions above the reaction vessels formed in the microplate 66. Then given amounts of the test samples sucked into the nozzles 57 to 60 are delivered into the reaction vessels by driving the syringes connected to the nozzles. If the blood cell test sample is to be delivered into four reaction vessels by the same amount, a fourth of the sucked sample is first delivered into a reaction vessel. Then, the motor 65 is driven to move the nozzles 57 to 60 leftward in FIG. 4 by one pitch and the tips of nozzles are positioned above next succeeding four reaction vessels.

The predetermined amounts of the test samples are delivered into the reaction vessels. In this embodiment, it is possible to deliver the blood cell test sample and the serum test sample sucked in the nozzles 60 and 59, respectively can be partially delivered into four reaction vessels. Therefore, the above operation is repeated four times. After the given delivery has been finished the nozzles 57 to 60 are moved into the initial sample sucking positions G to J, respectively. During this movement, the nozzles may be washed by means of any conventional washing mechanism.

Then, the belt 43 is moved by the given pitch and the relevant block 38 is brought into a washing position. In the washing position, there are provided four washing nozzles 67 which are connected to a washing device 68. The washing is effected in the following manner. At first the samples remained in the diluting vessels 39 to 42 are suck out via the nozzles 67 and then a washing liquid is discharged into the vessels through the nozzles. Next, the washing liquid is sucked out of the vessels 39 to 42 via the nozzles 67. Then the washing liquid remained in the vessels 39 to 42 is removed by drying the vessels. In this manner the diluting vessels can be used repeatedly.

According to the sample preparing and delivering mechanisms mentioned above, it is possible to obtain the blood cell test sample and serum sample which are sufficiently diluted with the diluent and have the precisely predetermined dilution ratios. Further, the activity of blood cells can be retained effectively, because the blood cells are scarcely made into contact with the ambient air.

Figure 9:
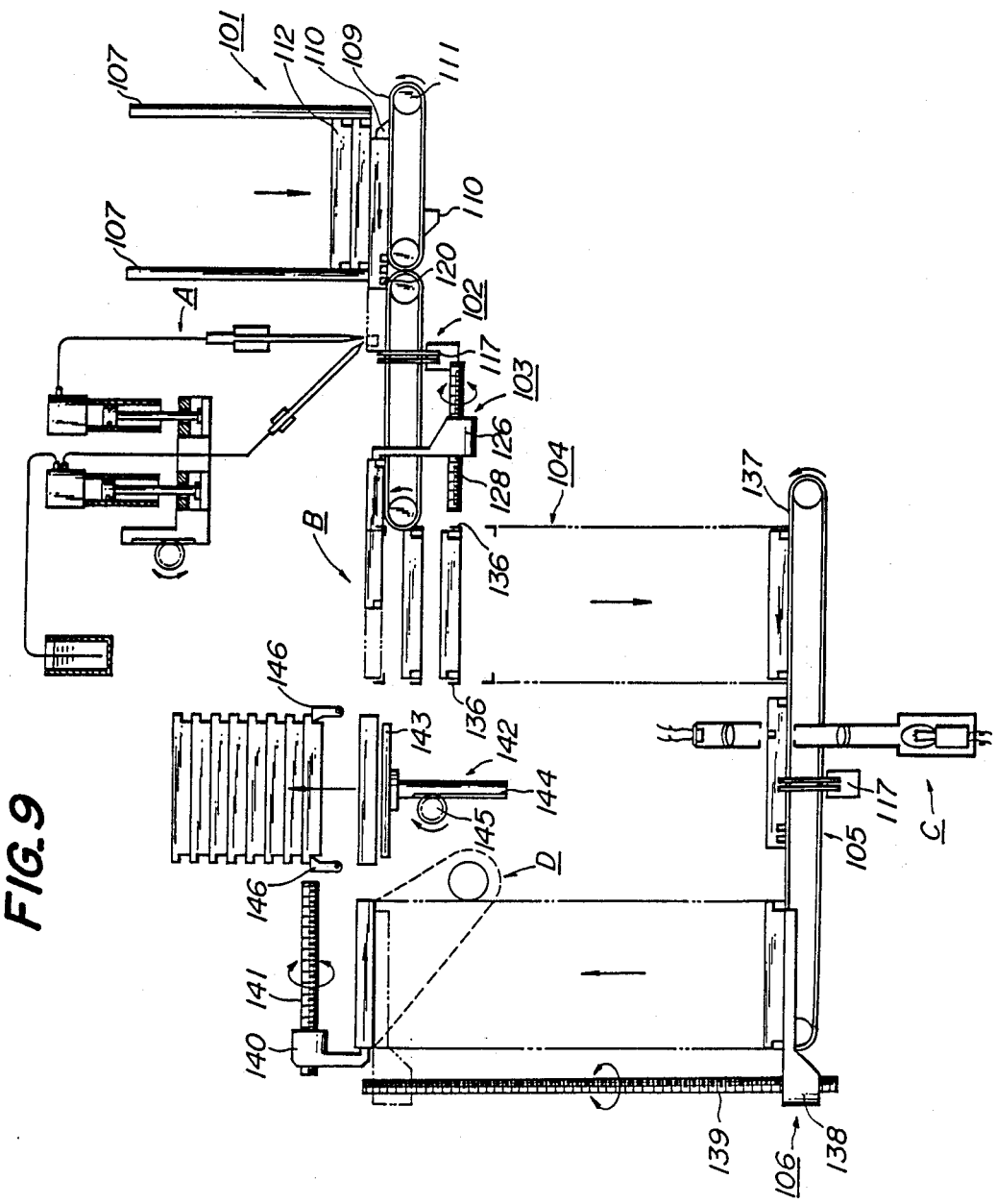
FIG. 9 is a diagrammatic side view showing construction of a part of the apparatus according to the present invention.

FIG. 9 shows the construction of microplate transporting device of the automatic blood analyzing apparatus according to the invention.

The microplate transporting device of the automatic blood analyzing apparatus according to the invention, as shown in FIG. 9, comprises a reagent delivery unit A for the microplate, a reaction line B for carrying out a reaction by holding the microplate after delivery, a measuring unit C for measuring a reaction result, and a visual observation portion D for monitor checking.

The microplate transporting device of the automatic blood analyzing apparatus further comprises a plate supply or feed means 101, a delivery transporting means 102, a first delivery means 103 for delivering the microplate to a reaction line, a reaction line transporting means 104, a measuring and transporting means 105, and a second delivery means 106 for delivering the microplate to a discharge position.

Figure 10:
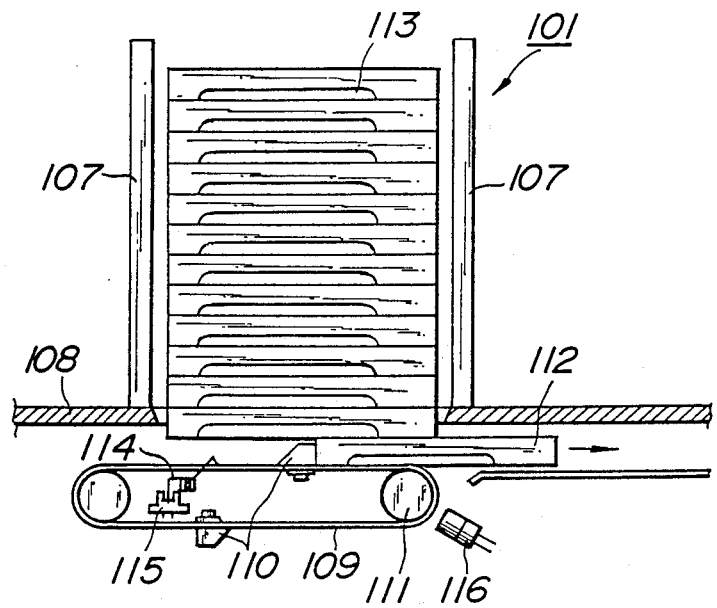
FIG. 10 is a side view illustrating microplate feeding means of the apparatus shown in FIG. 9.

The plate supply means 101 is provided with a guide 107 for enclosing four corners of the plate to a cover upper plate 108 (refer to FIG. 10) of the apparatus as a means for holding and receiving microplates in heaps. The plate supply means further has a pawl 110 projected to the outer surface of a single belt 109 and is provided with a belt driving means for driving a belt by a rotating drum 111. FIG. 10 shows a side surface opposite to the side surface of FIG. 9. As shown in FIG. 10, the plate supply means is provided with a direction detecting means having an operational arm 114 projected into a groove 113 formed on the side surface of a microplate 112. The arm is biased for usually detecting the other end portion opposite to the side projected into the groove 113 of the arm 114 by a direction detecting means 115. When the direction of the microplate is deviated by 180°, a small notch train different from the groove 113 shown in FIG. 10 is present on the side of the direction detecting means, and in this case, the arm 114 is rotated by engaging with the wall of the notch, and the other end portion is removed from the sensor 115 so as to generate an emergency signal to an operator. In order to step-drive the belt driving means, as shown in FIG. 10, a one-rotation detecting switch 116 is further provided. Till the pawl 110 is engaged with the rear surface of the ordinary faced microplate by rotation of the belt 109 and engaged with a pawl 117 of the stopping mechanism of the delivery transporting means 102, the microplate is pushed out along plate guide walls 118 on both sides of the microplate 112 and belts 119 on both sides of the bottom surface (refer to FIG. 11), so that a next microplate can be set on the belt 109.

Figure 11:
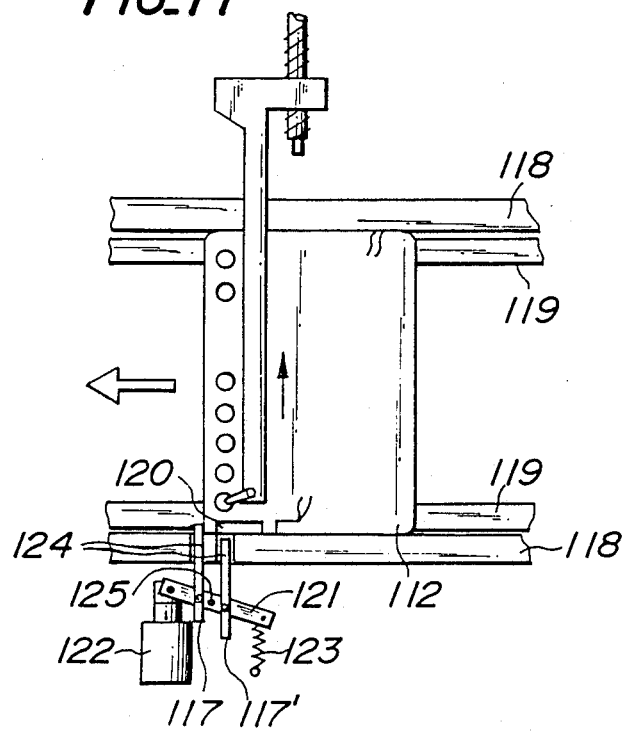
FIG. 11 is a plan view illustrating delivery transporting means of the apparatus shown in FIG. 9.

As shown in FIG. 11, the belt driving means of the delivery transporting unit has two belts 119 for supporting both sides of the bottom surface of the microplate, and the belts 119 are synchronized with each other so as to advance the plate along the guide wall 118 by every one pitch of the reaction vessel train. The delivery transporting means is provided with a stop mechanism for positively stopping the microplate by every one pitch, for example, the stop mechanism comprises stop pawls 117, 117' engaged with the notch wall by mutually injecting into a series of notches 120 formed on the side surface (left side viewed from the forward direction) of the microplate shown in FIG. 9, an operating lever 121, a solenoid 122 connected to one end of the operating lever, and a rest spring 123 connected to the other end of the operating lever, and a slidable guide 124 for injecting each stop pawl into the notch perpendicular to the forward direction of the plate is formed in one plate guide wall 118. The stop pawls 117, 117' are arranged on both sides of a fulcrum 125 of the lever 121. Then, the stop pawls 117' and 117 are alternately injected into the notch 120 by one energization or deenergization of the solenoid, and the plate forwards one pitch by driving the belt in this period. A pitch fed by belt driving and energization and deenergization of the solenoid is carried out after completing delivery of sample and reagent to all the reaction vessel trains at the delivery position by a delivery unit A'.

The stop pawl can be one, but in the case of one pawl, there is nothing to prevent the plate from moving when the solenoid is energized, so that if an accident occurs, the plate may move by larger pitch than one pitch. In order to prevent such movement, two pawls are provided for always injecting either pawl in the notch in either case of energization or deenergization of the solenoid.

As a first feeding means 103 for feeding the microplate after delivery to a reaction line along guide walls 118 and belts 119, a branch member 126 having a first arm 126' and a second arm 126" engaged with the rear surface of the microplate is mounted on a support 127, and the support 127 is mounted on a screw feed mechanism 128 (refer to (FIG. 12). In order to engage or disengage the first arm 126' with or from the plate rear surface, a slidable member provided at a free end of the second arm 126", a guide means 129 having a guide surface engaged with a ball bearing 126"a in the illustrated embodiment, is provided (refer to FIG. 13a).

The guide means 129 is provided with a guide rail 130 having the C-shaped cross section, and an inner surface of a flat portion of this guide rail is mounted a guide member 131 having a forward path guide surface and a backward path guide surface and one end adjacent to the end portion of the guide member is rotatably mounted a turning member 132 to the flat portion of the guide rail. This turning member is provided with a guide surface similar to the guide member and biased upward by a spring 133. The ball bearing 126"a of the second arm 126" is held between the guide surface of the guide member and the inner projected end of the guide rail 130.

At the end portion of the first arm 126' is secured a spring 134, the branch member 126 is rotated in the counterclockwise direction viewed from FIG. 13a, so as to engage the ball bearing 126"a with the upper inclined forward path guide surface. In this case, the first arm 126' is engaged with the rear surface of the microplate. When the ball bearing 126"a is slid along the forward path guide surface by rotating the screw feed mechanism 128 in the clockwise direction, the bearing is made into contact with the guide surface of the turning member 132 at the last portion of the forward route to rotate the turning member in the counterclockwise direction against the force of the spring 133, but is guided to the lower inclined backward path guide surface of the guide member along an inclined surface 132' of the turning member 132 (refer to FIG. 13b). The branch member is rotated in the clockwise direction against the force of the spring 134 an moved back to the initial position along the backward path guide surface by reverse rotation of the screw feed mechanism by taking the position disengaging from engagement with the plate (refer to FIG. 13b).

At the initial position, the guide member is not in the inside of the guide rail, so that the branch member is back to the condition of engagement with the rear surface of the plate by the spring 134.

Figure 14:
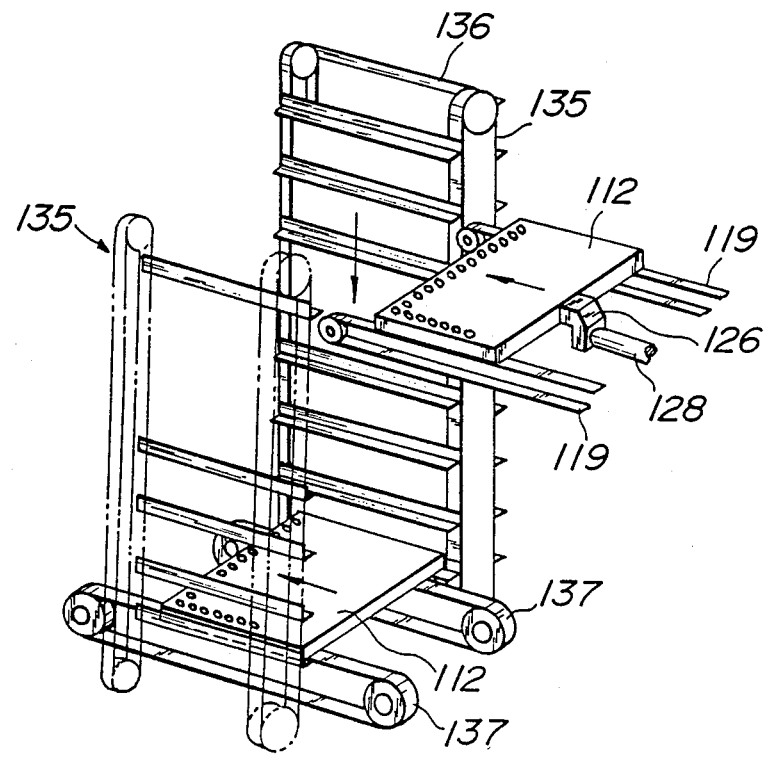
FIG. 14 is a diagrammatic perspective view showing the reaction transporting means.

The microplate then proceeds to the reaction line B', but according to the invention, the transporting means 104 of the reaction line comprises two circulating belt driving means 135 (refer to FIG. 14). A plurality of partition members 136 perpendicular from the driving surface in the driving direction of each circular belt are aligned on the driving surface by every gap slightly larger than the thickness of the plate, and driving axes on both sides of these circular belt driving means are arranged to extend on the horizontal and same perpendicular plane. Vertical planes inclusive of the driving axes of each circular belt driving means are opposed to each other in parallel, and the gap between the driving surfaces on the opposite sides from each other is made substantially equal to the width of the microplate. Further, in order to move the driving surface of the opposite side downward in the vertical direction and to move each partition member 136 by sucessively aligning on the same plane, intermittent driving is made. Successive microplates on the partition member intermittently and gradually lowered by synchronizing the belts 135 with each other are fed by the first feed means to reach the measuring transporting means after a predetermined reaction time.

When sending to the lowermost side by the circular belt driving means, the microplate is transferred onto a belt driving means 137 of the measuring transporting means 105 and sent to the measuring position before producing the next lowering. The construction of the measuring transporting means 105 is substantially the same as that of the delivery transporting means (refer to FIG. 11). Measurement is carried out by every reaction vessel row at the measuring position by the measuring unit C' (refer to FIG. 9).

The microplate after measurement is transferred to the carrier position by the second feed means 106. The second feed means 106, as shown in FIG. 9, comprises a first driving means having a support arm 138 for supporting the bottom surface of the microplate and a screw feed mechanism 139 for driving the support arm in the vertical direction, a second driving means having an engaging arm 140 for engaging with the front surface of the microplate at the perpendicular upper position and a screw feed mechanism 141 for driving the engaging arm in the horizontal direction, a push-up means 142 for pushing up the bottom surface of the microplate fed from the horizontal direction from the lower portion, and a detent means 146 for preventing the pushed-up microplate from lowering (refer to FIG. 9).

The push-up means 142 secures a push-up bar 144 with a rack to the lower surface of a support plate 143 for supporting the bottom surface of the microplate and pushes up the supporting plate 143 and the microplate by rotation of a pinion 145 meshed with the rack. When the plate is pushed up against the inner pressure force of an elastic member (not shown) of the detent means 146, the detent means is restored inward by elastic force, injected into the notch of the plate bottom surface, supports the plate by the upper surface of the detent means and successively superimposes the plates after measurement from the bottom. After stacking the plates to some extent, an operator can carried them out.

Figure 15:
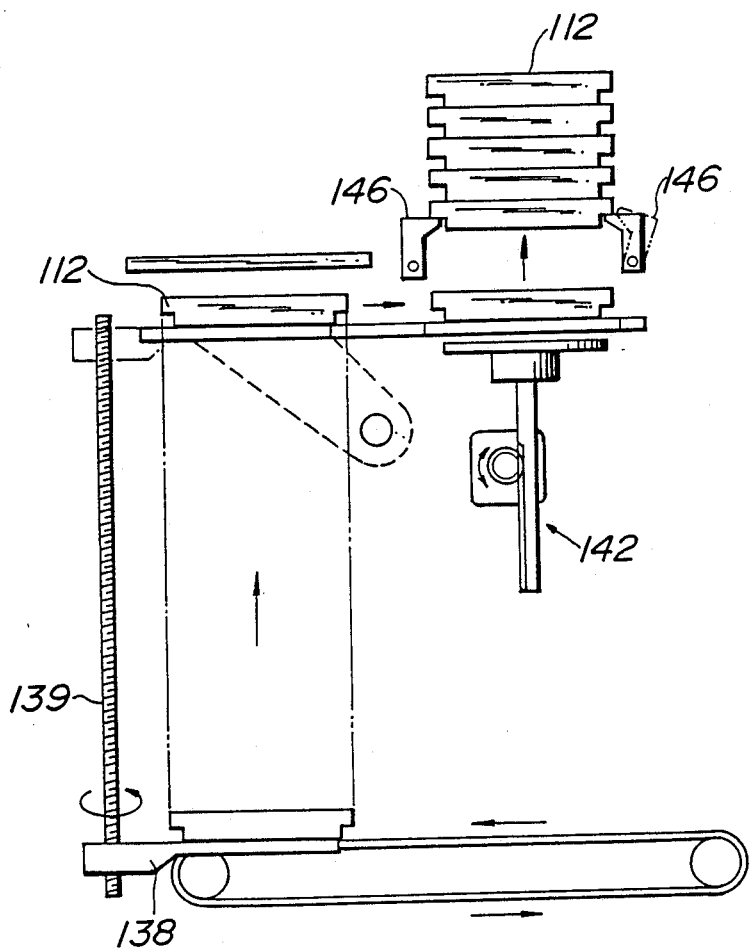
FIG. 15 is a diagrammatic side view illustrating second sending means for supplying to the discharge position the observed microplate of the apparatus shown in FIG. 9.

As disclosed in FIG. 15, it is convenient to monitor check by a visual observation unit D' at the position fed from the first driving means to the vertical upper portion. Therefore, the support arm 138 is formed with a translucent member for such observation.

According to the above construction, the automatic blood analyzing apparatus of the present invention can feed the plate by the guide as shown in FIG. 10, so as to optionally add plates and easily confirm remaining plates and further confirm direction by the eye. The plates in the reaction line are separately stacked in the perpendicular direction by means of partition members, so that an occupied area of the reaction line can be made small so as to miniaturize the apparatus, and so that vibrating is minimized, and as a result, reaction result becomes good. In addition, supply and carrier of the plates are firstin-firstout, so that it is not necessary to rearrange at the final check, but a successive check is sufficient.

The present invention is not limited to the above mentioned embodiments, but may be modified in various manners without departing from the scope of the invention.

What is claimed is:

1. An immunological agglutination reaction analyzing apparatus comprising:
   a microplate carrying line including, in sequence, a microplate feeding line, a reagent delivery transporting line, a microplate sending line, a reaction transporting line, a measurement transporting line and a microplate discharging line, said microplate sending line, said reaction transporting line and said measurement transporting line together forming a reaction line;
   a plurality of sample tubes;
   means for carrying said plurality of sample tubes along a sample carrying line to successively place said sample tubes at a first delivery position, said sample tubes containing blood samples to be analyzed, said means for carrying a plurality of sample tubes comprising:
   a plurality of removable racks;
   a cassette tray having a plurality of partitions successively arranged at spaced distances to define a plurality of gaps, each gap being constructed to receive a removable rack containing a plurality of sample tubes;
   means for receiving said cassette tray and for intermittently advancing said cassette tray towards a discharge position, said cassette tray being advanced by the distance between adjacent partitions for each intermittent advance and presenting racks successively at a feed position;
   means for moving a rack selected from a gap of a cassette tray located at said feed position after each intermittent advance and transporting that rack to position its sample tubes at said first delivery position; and
   means for returning the selected rack to said gap of the cassette tray located at said feed position prior to the next advance;
   means for forming a plurality of diluted blood samples by transferring a blood sample from each sample tube at the first delivery position to a respective diluting tube located at a beginning end of a diluted blood sample carrying line, and by adding diluent to each respective diluting tube, said means for forming a plurality of diluted blood samples comprising, a plurality of diluting tubes, means for delivering a blood sample contained in a sample tube into a plurality of diluting tubes and means for discharging diluent solutions into each respective diluting tube at the same time or before a blood sample is delivered therein from a sample tube to form diluted blood samples;
   means for carrying the diluted blood samples within the diluting tubes along said diluted blood sample carrying line to a position adjacent a beginning end of said microplate sending line;
   a plurality of microplates;
   means for successively feeding said plurality of microplates to the beginning end of said reagent delivery transporting line from said microplate feeding line, each of said microplates including a plurality of reaction vessels therein, said microplate feeding means comprising:
   means for holding a vertical stack of said plurality of microplates;
   belt drive means having a belt for receiving the lowest microplate from the stack and a claw for engaging a rear surface of a received microplate; and means engaging a channel in a side surface of a microplate for detecting a direction of orientation of the microplate;
   first transporting means for transporting said microplates in a horizontal direction along said reagent delivery transporting line to a reagent delivery position at said beginning end of said microplate sending line;
   means disposed adjacent said reagent delivery position for delivering given amounts of the diluted blood samples from the diluting tubes in said diluted blood sample carrying line into at least one reaction vessel of said microplates positioned at the beginning end of said microplate sending line;
   means disposed adjacent said reagent delivery position for delivering given amounts of reagents into said at least one reaction vessel at the beginning end of said microplate sending line in accordance with an analysis to be performed;
   first sending means for sending microplates with reaction vessels having said diluted blood samples and reagent contained therein in a horizontal direction along said microplate sending line to the beginning end of said reaction transporting line;
   means for lowering said microplates with reaction vessels vertically in a stacked configuration along said reaction transporting line to the beginning end of said measurement transporting line in a substantially non-vibrating manner such that antigen and antibody combination reactions may occur in said at least one reaction vessel as a result of the receipt of said diluted blood sample and reagent in said at least one reaction vessel to form an agglutination pattern on a bottom surface of said reaction vessel, said means for lowering said microplates comprising,
   first circulating belt drive means having a belt defining a drive axis which extends in the vertical direction and a plurality of partition members disposed on said belt orthogonal to said drive axis and equidistant from one another,
   second circulating belt drive means having a belt defining a drive axis which extends in the vertical direction and a plurality of partition members disposed on said belt orthogonal to said drive axis and equidistant from one another, said first and second circulating belt drive means being positioned in opposed relation such that the vertical planes including the drive axis of each circulating belt drive means are parallel to one another and separated by a distance equal to the width of a microplate and such that each partition on one belt of a circulating drive means is in the same horizontal plane as a partition on the belt of the opposed circulating drive means along the length of the drive axis to form pairs of opposed partitions, and means for synchronously moving the belts of said circulating belt drive means to intermittently move said opposed partitions vertically while maintaining said horizontal plane, said circulating belt drive means being positioned such that microplates are received by said pairs of opposed partitions from said microplates sending line in a horizontal position and thereafter moved vertically;

second transporting means for transporting said at least one reaction vessel having agglutination patterns formed on a bottom surface thereof horizontally along said measurement transporting line to a measuring position;

means for photoelectrically detecting agglutination patterns formed on said bottom surface of said at least one reaction vessel at said measuring position to thereby produce a detection signal;

means for receiving said detection signal to effect an analysis as a result of a detected signal agglutination pattern;

second sending means for horizontally sending microplates after measurement to a raised position; and means for discharging said microplates along said microplate discharging line from said raised position after visual observation of the agglutination patterns in all reaction vessels of one microplate.

2. The apparatus of claim 1 wherein said means for forming a plurality of diluted blood samples includes means for forming a blood cell suspension used for immunological agglutination reactions, said means for forming a blood cell suspension including means for delivering diluent solution and blood cell solutions to a diluting vessel in such a manner that the delivery of the diluent solution begins prior to or simultaneous with the delivery of the blood cell solution to the diluting vessel.

3. The apparatus of claim 1 wherein said fist transporting means and said second transporting means each includes belt drive means having a belt for transporting microplates between guide walls for intermittently advancing said groups of reaction vessels in a microplate by a predetermined distance and stopping means having a claw for engaging notches formed in a side of a microplate for surely stopping microplate movement after each advance.

4. The apparatus of claim 1 wherein said first sending means comprises:

a support member;

a branch member pivotally coupled to said support member and having a first arm engageable with a rear surface of a microplate and a second arm having a slidable member;

drive means for reciprocally moving the support member to linearly push microplates along guide walls of the reaction line when said first arm is enagaged with the rear surface of a microplate;

guide means for guiding said slidable member including a forward path guide surface and a backward path guide surface which engage said slidable member, said slidable member causing said first arm to engage said microplate during engagement of said slidable member with said forward path guide surface and causing said first arm to disengage said microplate during engagement of said slidable member with said backward path guide surface and means for causing said slidable member to change engagement from said forward path guide surface to said backward path guide surface; and return means for moving said second arm such that the slidable member moves from engagement with said backward path guide surface to said forward path guide surface.

5. The apparatus of claim 1 wherein said means for discharging microplates comprises:

first drive means having a supporting arm for supporting a bottom surface of a microplate and driving the microplate in a vertical direction; and second drive means having an engaging arm for engaging a front surface of a microplate and driving a microplate in a horizontal direction; and wherein said means for discharging comprises:

means for pushing on the bottom surface of a microplate received from said second drive means to move said microplate in a vertical upward direction; and detent means for receiving and holding a microplate pushed in said vertical upward direction.

6. The apparatus of claim 1 wherein said means for discharging microplates includes means for allowing visual observation of said microplates prior to discharge.

* * * * *